United States Patent [19]

Tobin

[11] Patent Number: 4,858,476
[45] Date of Patent: Aug. 22, 1989

[54] BREATHING ZONE AIR SAMPLER

[75] Inventor: John Tobin, Bethel Park, Pa.

[73] Assignee: The United States of America as represented by the United States Department of Energy, Washington, D.C.

[21] Appl. No.: 147,823

[22] Filed: Jan. 25, 1988

[51] Int. Cl.⁴ .......................... G01N 1/24; G01N 1/26
[52] U.S. Cl. .............. 73/863.23; 73/863.33; 73/864.73; 351/158
[58] Field of Search ........... 73/863.23, 863.25, 863.31, 73/863.33, 864.34, 864.73; 351/158

[56] References Cited

U.S. PATENT DOCUMENTS

| | | | |
|---|---|---|---|
| 2,245,969 | 6/1941 | Francisco et al. | 128/207.18 |
| 4,080,832 | 3/1978 | Moody et al. | 73/863.23 |
| 4,350,507 | 9/1982 | Greenough et al. | 73/863.23 X |
| 4,360,253 | 11/1982 | Wyatt | 351/158 |
| 4,389,903 | 6/1983 | Bertone et al. | 73/863.23 X |
| 4,465,067 | 8/1984 | Koch et al. | 128/207.18 |
| 4,559,941 | 12/1985 | Timmons et al. | 128/207.18 |
| 4,589,292 | 5/1986 | Delhaye et al. | 73/863.23 X |
| 4,721,517 | 1/1988 | Cloutier | 73/863.23 |

FOREIGN PATENT DOCUMENTS 2233660  1/1974  Fed. Rep. of Germany .

*Primary Examiner*—Tom Noland
*Attorney, Agent, or Firm*—William W. Randolph; Judson R. Hightower; Richard E. Constant

[57] ABSTRACT

A sampling apparatus is provided which comprises a sampler for sampling air in the breathing zone of a wearer of the apparatus and a support for the sampler preferably in the form of a pair of eyeglasses. The sampler comprises a sampling assembly supported on the frame of the eyeglasses and including a pair of sample transport tubes which are suspended, in use, centrally of the frame so as to be disposed on opposite sides of the nose of the wearer and which each include an inlet therein that, in use, is disposed adjacent to a respective nostril of the nose of the wearer. A filter holder connected to sample transport tubes supports a removable filter for filtering out particulate material in the air sampled by the apparatus. The sample apparatus is connected to a pump for drawing air into the apparatus through the tube inlets so that the air passes through the filter.

2 Claims, 1 Drawing Sheet

BREATHING ZONE AIR SAMPLER

FIELD OF THE INVENTION

The present invention relates to sampling devices for sampling the air in environments which are suspected of being contaminated with airborne toxic particles.

BACKGROUND OF THE INVENTION

An accurate evaluation of the exposure of a worker to concentrations of toxic airborne particulate material requires a sampling technique which produces a representative sample of the airborne particulate concentration existing in the air actually breathed by the worker.

Presently, breathing zone sampling is carried out using an open-faced filter assembly that clips to the lapel of a worker. One example of such a sampling arrangement is disclosed in U.S. Pat. No. 4,389,903 (Bertone et al.) wherein a filter unit is clipped to the collar of a miner or other worker and is connected by a conduit to a pump housed in a unit clamped to the belt of the worker. Because the concentration of airborne particulates can vary appreciably over very short distances, i.e., distances as small as several inches, the spacing between such a lapel sampler filter and the actual breathing zone of the worker can lead to results which are not truly representative, i.e., results which do not accurately portray the actual particulate concentrations experienced by the worker. In addition, such lapel sampler filters are typically orientated vertically, so that air flow detected is horizontal which is different from the vertical upward flow into the nose of worker. Further, the velocity of the sampled air entering the filter media rarely, if ever, matches the velocity of the air entering the nose of the worker.

SUMMARY OF THE INVENTION

In accordance with the invention a breathing zone sampling apparatus is provided which overcomes the above-discussed deficiencies of the lapel samplers presently in use for this purpose, thereby reducing or eliminating the sampling errors which inherently result with the use of such prior art samplers.

Broadly speaking, the breathing zone sampling apparatus or sampler of the invention includes at least one transport tube connected to a filter assembly and disposed so that the inlet to the transport tube is located in the breathing zone of a wearer of the device. The sampler is preferably attached to the frames of a pair of eyeglasses worn by the user, or formed as an integral part of such eyeglass frames, so that the transport tube or tubes (two of such tubes are used in a preferred embodiment) can be readily disposed in the breathing zone of the worker wearing the glasses.

A further advantage of this attachment or support arrangement is that the inlet of the sample transport tube (or tubes) follows the head movement of the wearer and is thus retained in position relative to the breathing zone of the worker. It will be appreciated that this is not true of the lapel samplers currently in use.

In addition, the sampling apparatus of the invention can be constructed so as to operate at an air flow rate which substantially duplicates that of normal breathing, and with the sample transport tubes orientated in a manner similar to the orientation of the nostrils. These features in combination with the location of the sample tube inlet(s) in the breathing zone, i.e., in proximity to the nostrils, results in an air sample which accurately represents that to which the worker is exposed, in contrast to lapel-type samplers which suffer the shortcomings discussed above.

In accordance with a preferred embodiment of the present invention, a sampling device is provided which is mounted on the frames of a pair of eyeglasses for sampling the air in the breathing zone of a wearer of the eyeglasses, the sampling device comprising sampling means, supported on the frame of the eyeglasses and extending into the breathing zone of a wearer of the eyeglasses, for obtaining samples of the air in the area of the nostrils of a wearer of the eyeglasses; a filter means, connected to the sampling means, for filtering out particulate matter contained in the air sampled by the sampling means; and pump means, connected to the filter means, for drawing air into the sampling means and through the filter means. The sampling means preferably comprises a pair of sample transport tubes extending downwardly from the frame and having sampling inlets adapted to be disposed in proximity to the nostrils of a wearer of the eyeglasses. Advantageously, the filter means comprises a filter holder supported on the frame of the eyeglasses and a removable filter removably mounted in the filter holder.

Other features and advantages of the invention will be set forth in, or apparent from, the detailed description of the preferred embodiments of the invention which follows.

DESCRIPTION OF THE PREFERRED EMBODIMENTS

Figure 2:
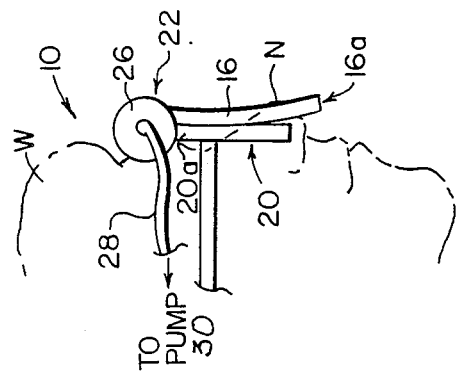
FIG. 2 is a side elevational view of the sampling apparatus of FIG. 1.
Figure 1:
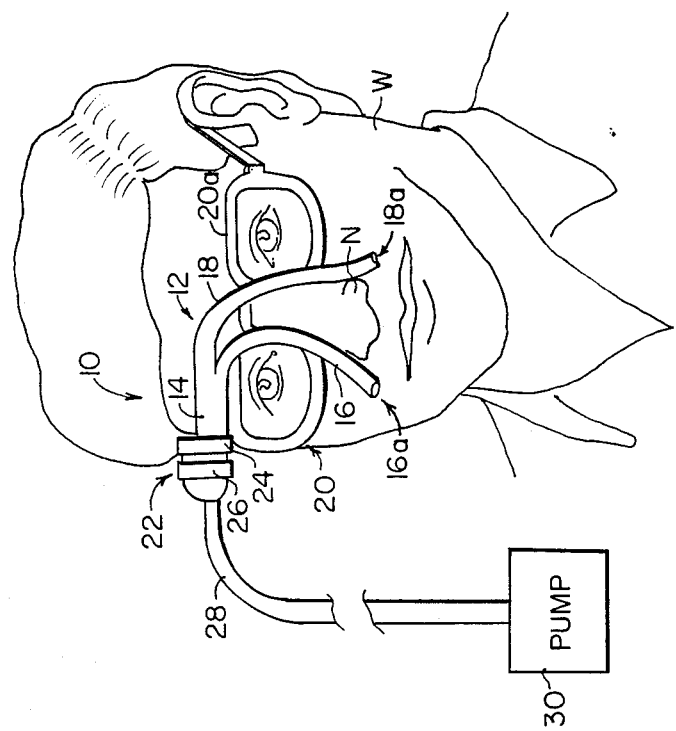
FIG. 1 is a perspective view of the sampling apparatus of the invention, showing the apparatus in place on a wearer.

Referring to FIG. 1, a sampling apparatus, constructed in accordance with a preferred embodiment of the invention, is generally denoted 10. The apparatus 10 includes a sampling assembly 12 including a main body portion 14 which is connected a pair of sample transport tubes 16 and 18 having respective inlets 16a and 18a at the free ends thereof. As illustrated, tubes 16 and 18 are located on opposite sides of the nose, denoted N, of a wearer, denoted W, and the respective inlets 16a and 18a are disposed adjacent to the nostrils of the wearer. Thus, apparatus 10 is able to obtain air samples directly from the breathing zone of the wearer, i.e., to obtain samples of air which are very similar to the air actually breathed by the wearer.

The sampling assembly 12 of sampling apparatus 10 is mounted on the frames 20a of a pair of eyeglasses, generally denoted 20, along the top thereof so that the tubes 16 and 18 are disposed along the sides of the nose N of wearer W as described above. It should be noted that the sampling assembly 12 can be adapted to be attached to existing eyeglasses by suitable clips or other attachment means (not shown) or can be formed integrally with the eyeglasses 20 in which case the eyeglasses can be provided with either corrective or clear lenses.

The main body portion 14 of sampling assembly 12 is connected to a filter assembly 22 including a filter holder 24 in which a filter 26 is removably mounted. Filter 26 is designed to filter out particulate matter, including toxic materials, in the air samples and can be removed for inspection from time-to-time, as desired. The removable filter 26 and associated filter holder 24 can, of course, take a number of different conventional forms.

The filter assembly 22 is connected by a suitable tubing 28 to a pump 30. Pump 30 is preferably a conventional, commercially available, portable, battery operated vacuum pump which provides the necessary vacuum source for drawing the air through the transport tubes 16 and 18 to the filter assembly 22 so as to provide collection of particulates during in-field testing in suspect environments.

With the construction of the sampling apparatus of the invention described above, the apparatus can be made so as to operate at an inlet sampling flow rate that duplicates the flow rate at the nostrils of a worker. Further, locating the sampling inlets 16a and 18a as described above, and illustrated in FIG. 1, also simulates the normal air flow orientation associated with normal breathing. Sampling in close proximity to the breathing zone, at approximately the same flow rate and orientation as normal breathing, results in an air sample that accurately represents the airborne concentration to which the worker is exposed. As discussed above, existing lapel-type samplers do not truly sample the breathing zone and the sample flow rate and inlet orientation associated with such samplers do not accurately duplicate normal breathing conditions.

Although the invention has been described relative to exemplary embodiments thereof, it will be understood by those skilled in this art that variations and modifications can be effected in these exemplary embodiments without departing from the scope and spirit of the invention.

I claim:

1. A sampling apparatus comprising sampling means for sampling air in the breathing zone of a wearer of the apparatus and support means for said sampling means comprising a pair of eyeglasses including a frame; said sampling means comprising a sampling tube supported on the frame of said eyeglasses and including a main body portion and a pair of sample transport tubes connected to said main portion and suspended, in use, therefrom centrally of said frame so as to be disposed on opposite sides of the nose of the wearer in close proximity but spaced therefrom so that a representative sample of air breathed by the wearer can be taken without obstructing the flow of air into the nostrils of the wearer, said transport tubes each including an inlet therein which, in use, is disposed adjacent to a respective nostil of the nose of the wearer; a filter holder connected to said main body portion of said sample tube; a filter removably mounted in said filter holder for filtering out particulate material in the air sampled by the apparatus; and means for connecting the sampling apparatus to a pump for drawing air into the apparatus through said inlets so that the air passes through said filter.

2. In combination with a pair of eyeglasses, a sampling device for sampling the air in the breathing zone of a wearer of the eyeglasses, said sampling device comprising sampling means, supported on the frame of said eyeglasses and extending into the breathing zone of a wearer of the eyeglasses, for obtaining samples of the air in the area of the nostrils of a wearer of the eyeglasses, wherein said sampling means comprises a pair of transport tubes extending downwardly from said frame and having sampling inlets adapted to be disposed in close proximity to the nostrils of a wearer of the eyeglasses to simulate the position of the nostrils of the wearer of the eyeglasses so that a representative sample of air breathed by the wearer of the eyeglasses can be taken without obstructing the flow of air into the nostrils of the wearer of the eyeglasses, a filter means connected to said sampling means for filtering out particulate matter contained in the air sampled by said sampling means, and pump means connected to said filter means for drawing air into said sampling means through said filter means.

* * * * *